(12) United States Patent
Park et al.

(10) Patent No.: US 12,422,392 B2
(45) Date of Patent: Sep. 23, 2025

(54) GAS SENSOR DEVICE BASED ON METAL OXIDE FOAM

(71) Applicant: CellMo Materials Innovation, Inc., Berkeley, CA (US)

(72) Inventors: Hyeji Park, Seoul (KR); Hee Chul Lee, Gyeonggi-do (KR); Gigap Han, Chungcheongnam-do (KR); Heeman Choe, Conroe, TX (US)

(73) Assignee: CellMo Materials and Innovation, Inc., Conroe, TX (US)

( * ) Notice: Subject to any disclaimer, the term of this patent is extended or adjusted under 35 U.S.C. 154(b) by 577 days.

(21) Appl. No.: 17/441,198

(22) PCT Filed: Mar. 26, 2020

(86) PCT No.: PCT/US2020/025071
§ 371 (c)(1),
(2) Date: Sep. 20, 2021

(87) PCT Pub. No.: WO2020/198533
PCT Pub. Date: Oct. 1, 2020

(65) Prior Publication Data
US 2022/0155247 A1 May 19, 2022

Related U.S. Application Data

(60) Provisional application No. 62/824,276, filed on Mar. 26, 2019.

(51) Int. Cl.
*G01N 27/12* (2006.01)
*C01G 19/02* (2006.01)
(Continued)

(52) U.S. Cl.
CPC ........... *G01N 27/125* (2013.01); *C01G 19/02* (2013.01); *G01N 27/407* (2013.01); *B28B 1/007* (2013.01); *C01P 2002/72* (2013.01)

(58) Field of Classification Search
CPC .. G01N 27/125; G01N 27/407; G01N 33/004; C01G 19/02; B28B 1/007; C01P 2002/72; B22F 7/064; B22F 7/08
See application file for complete search history.

(56) References Cited

U.S. PATENT DOCUMENTS

| 5,755,940 A * | 5/1998 | Shindo | ................. G01N 33/004 204/426 |
| 2014/0071645 A1* | 3/2014 | Glanz | ..................... H01L 23/15 427/58 |

(Continued)

OTHER PUBLICATIONS

Nam, Kyungju et al., Morphology and Gas-Sensing Properties of Tin Oxide Foams with Dual Pore Structure, Journal of Electronic Materials, Jan. 24, 2017, pp. 3748-3756, vol. 46, 2017 The Minerals, Metals, & Materials Society. (Year: 2017).*

(Continued)

*Primary Examiner* — Freddie Kirkland, III
(74) *Attorney, Agent, or Firm* — Aka Chan LLP

(57) ABSTRACT

A gas sensing device is manufactured with three dimensionally connected metal oxide foam structure of large surface area and elongated channel pores within the three-dimensional porous structure for gas sensing applications, thereby increasing the surface area of the sensing layer and expediting sensitivity and sensor response. A gas sensor device includes the fabricated metal-oxide-foam sensing material attached via silver paste to platinum electrodes and ruthenium heater that are printed on low temperature co-fired ceramic substrate. This device will provide improved gas sensing performance with improved sensitivity and response time. Gas sensors including the metal oxide foam sensing material exhibit higher sensitivity to toxic gases such as ethanol and carbon monoxide due to the large surface area achieved from the porous three-dimensional structure providing increased chemical reaction sites and the larger (Continued)

porous channels allowing gases to easily pass, shortening the gas diffusion reaction path.

20 Claims, 12 Drawing Sheets

(51) Int. Cl.
*G01N 27/407* (2006.01)
*B28B 1/00* (2006.01)

(56) References Cited

U.S. PATENT DOCUMENTS

2015/0072236 A1* 3/2015 Um ................... H01M 4/1395
                                                    429/231.95
2018/0038816 A1* 2/2018 Hsiao ................. G01N 33/004

OTHER PUBLICATIONS

Ma, Mingsheng et al., A novel wireless gas sensor based on LTCC technology, Sensors and Actuators B: Chemical, Aug. 13, 2016, pp. 711-717, 2016 Elsevier B.V. (Year: 2016).*
Samerjai, T., et al., "Flame-spray-made metal-loaded semiconducting metal oxides thick films for flammable gas sensing," Sensors and Actuators B, vols. 171-172, pp. 43-61, 2012.

* cited by examiner

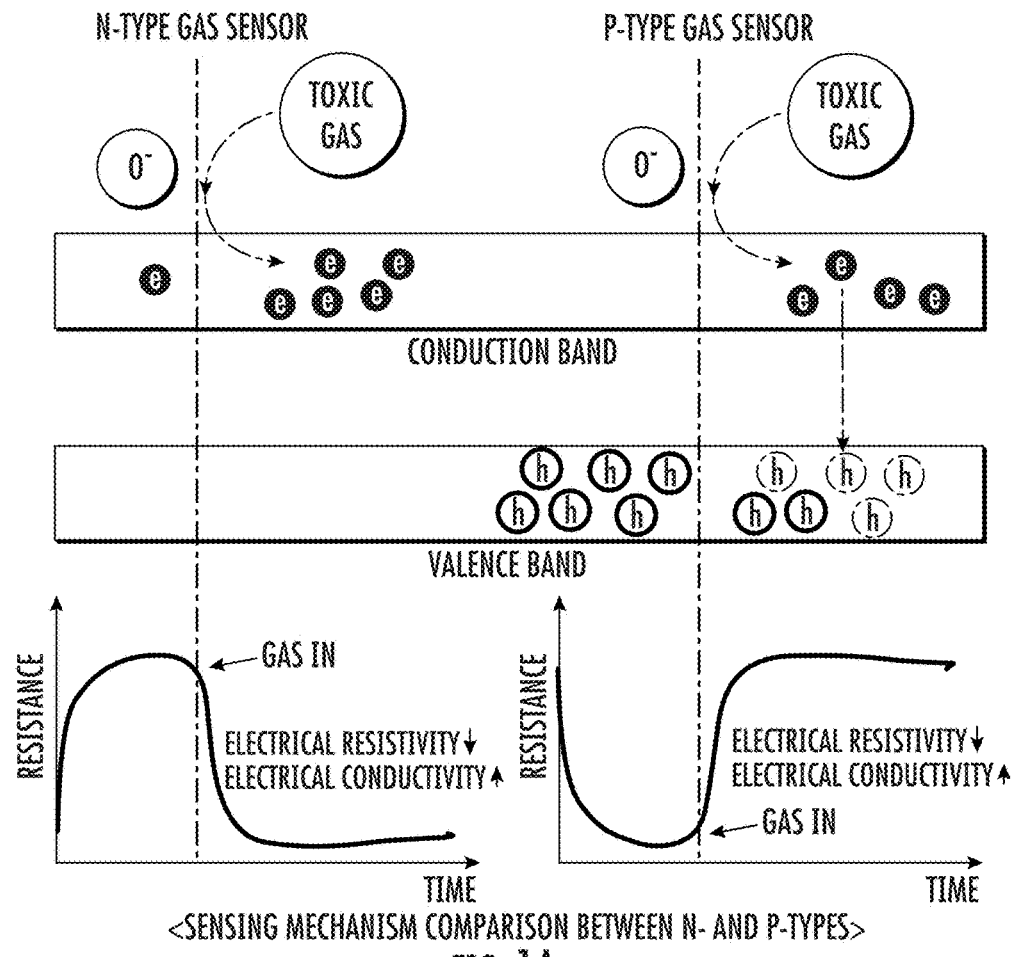
FIG. 1A
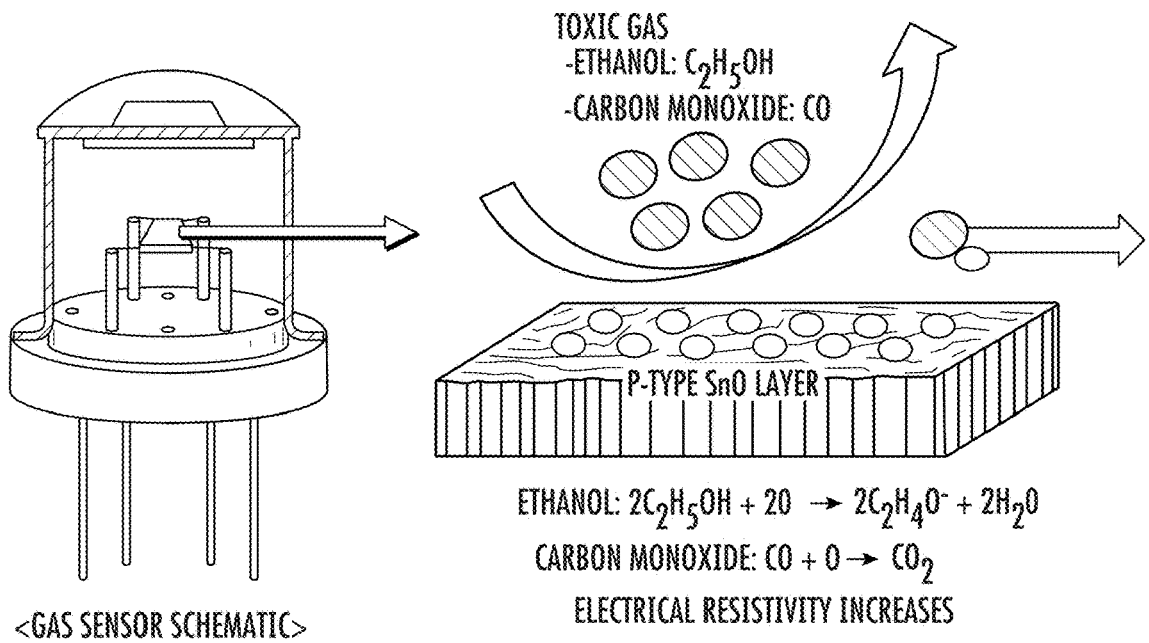
FIG. 1B
FIG. 1C

FIG. 4B
FIG. 4F
NATURAL TOP VIEW IMAGES

FRACTURED CROSS SECTIONAL IMAGES $CuO_{(s)} + CO_{(g)} \rightarrow Cu_{(s)} + CO_{2(g)}$ $2CuO_{(s)} + CO_{(g)} \rightarrow Cu_2O_{(s)} + CO_{2(g)}$ (1) GREEN SHEET CASTING AND BLANKING (4 LTCC LAYERS)

(2) VIA PUNCHING AND FILING (3) SCREEN PRINTED RuO2 HEATER FORMATION AND TERMINATION (4) TOP LTCC (1 LAYER) SENSOR ELECTRODES WITH VIA PUNCHING AND FILLING (5) INERT LAYER FOR ZERO SHRINKAGE (6) CO-FIRING AND DICING (7) ATTACHMENT OF METAL OXIDE FOAM SENSOR

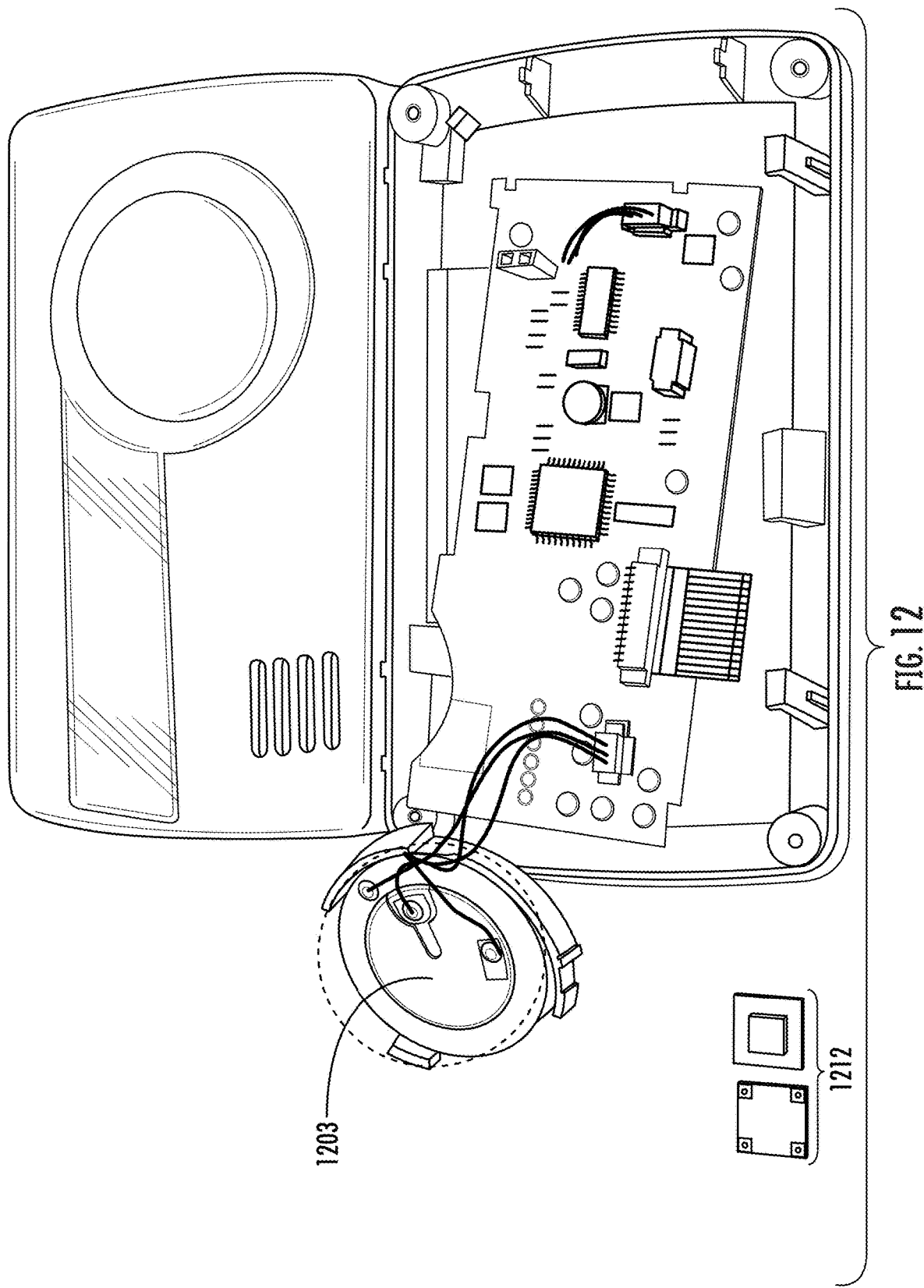

GAS SENSOR DEVICE BASED ON METAL OXIDE FOAM

CROSS-REFERENCE TO RELATED APPLICATIONS

This patent application claims the benefit of U.S. patent application 62/824,276, filed Mar. 26, 2019, which is incorporated by reference along with all other references cited in this application.

BACKGROUND OF THE INVENTION

The invention relates to the field of gas-sensing device technology. More specifically, this invention is to develop a sensitive gas detection device using metal oxide foam to effectively monitor a variety of toxic gases with appropriate gas sensors, which can detect the presence of a toxic gas at very low to high particle concentrations with greater sensitivity and shorter sensing time.

Technical difficulties arise because most toxic gases are present at relatively low concentration. It is very important to select an appropriate sensing material that shows an accurate sensitive response to the target gas at low concentration. It is also important to use a gas sensor device with a shorter sensing time where the target gas can go in and out as quickly as possible.

There are a variety of industrial and private sectors desperately demanding advanced gas-sensing technology. For example, with dramatic advances in modern technology, numerous toxic gases are being produced, and there is growing concern about accidental leakages, where those gases can seriously affect the environment and both human and animal health. In addition, a new regulation in the United States requires that every new building should be equipped with a carbon monoxide detector to prevent fire hazards.

Therefore, there is a need for improved gas-sensing device technology and materials.

BRIEF SUMMARY OF THE INVENTION

A new gas sensing device is manufactured with three dimensionally connected metal oxide foam structure of large surface area and elongated channel pores within the three-dimensional porous structure for gas sensing applications, thereby increasing the surface area of the sensing layer and expediting sensitivity and sensor response. The gas sensor device includes the fabricated metal-oxide-foam sensing material attached via silver paste to platinum electrodes and a ruthenium heater that are printed on low temperature co-fired ceramic substrate. This device will provide improved gas sensing performance with improved sensitivity and response time (e.g., quicker gas in and out). Gas sensors including the metal oxide foam sensing material exhibit higher sensitivity to toxic gases such as ethanol and carbon monoxide due to the large surface area achieved from the porous three-dimensional structure providing increased chemical reaction sites and the larger porous channels allowing gases to easily pass, shortening the gas diffusion reaction path.

The method is explained explicitly based on the results of tin oxide gas sensing material, but can be extended to many other metal oxides, and includes fabrication of metal oxide foam with pore sizes ranging from several hundred nanometers to several tens of micrometers and applying these as the sensing material for gas sensor applications. The manufactured metal oxide foam reacts with toxic gases across its extended surface layer when exposed to the target gas.

A new method of manufacturing three-dimensional metal oxide foam (e.g., tin oxide and copper oxide foams as examples) for use as an advanced gas sensing material. The method consists of manufacturing tin oxide foam with pore sizes ranging from several hundred nanometers to a few micrometers for use as the gas sensing material, then patterning two electrode pads at 200-micron spacing by a lift-off process using a shadow mask on the metal oxide foam.

Gas sensors including the porous tin oxide foam exhibit higher sensitivity to toxic gases such as ethanol and carbon monoxide due to the large surface area achieved from the porous three-dimensional structure providing increased chemical reaction sites and the larger porous channels allowing gases to easily pass, shortening the gas diffusion reaction path.

Tin oxide is a commonly used gas sensing material that can be applied for n or p-type gas sensors, depending on its crystal structure. This patent details fabrication of tin oxide and other metal oxide foams using a new method combining slurry foaming and powder sintering to provide an improved sensitivity gas sensing material. Tin oxide foams fabricated using the method detailed in this patent showed different morphological features depending on major processing parameters, including sintering temperature, sintering time, and the amount of added powder. Scanning electron microscopy images identified a dual pore structure within the tin oxide foam containing arrays of 5.3-10.7 micron pores, as well as smaller secondary pores of a few microns diameter on the wall surfaces. Gas sensing performance for the synthesized tin oxide foams in a relatively large experimental chamber showed 13.1 sensitivity, 192 seconds response time, and 160 seconds recovery time for 600 parts per million ethanol gas at 300 degrees Celsius; and 35.9 seconds, 39 seconds, and 27 seconds, respectively, for 5000 parts per million carbon monoxide gas at 200 degrees Celsius. This is a remarkable detection result given that the samples fabricated following the current patent had no addition of catalyst.

Additionally, freeze-cast copper oxide foam at low carbon monoxide concentrations of from 1000 ppm to 5000 ppm at 300 degrees Celsius exhibits steadily increasing sensitivity of copper oxide foam with increasing carbon monoxide gas concentration, confirming the metal oxide sensor structure is beneficial for detecting toxic gases such as carbon monoxide with its enhanced sensing surface area. A metal oxide foam gas sensor device was manufactured, where platinum electrodes and ruthenium oxide heater are printed on Low Temperature Co-fired Ceramic (LTCC) substrate before the metal oxide foam sensor was attached on top of the heater and electrodes using Ag paste. This sensor device can directly replace the existing sensing material component.

In an implementation, a gas sensor device includes a metal-oxide-foam sensing material coupled via silver paste to platinum electrodes and ruthenium heater that are printed on LTCC. The electrode pattern can include two electrode pads of a suitable metal, such as platinum, with spacing of a few hundred micrometers using a lift-off process and shadow mask for use as the electrodes of the attached metal oxide foam sensor.

The metal oxide foam has a porosity between about 55 percent and about 90 percent and is a gas sensing material in a sensor device, which reacts with specific target (e.g., toxic) gases, such as ethanol, carbon monoxide, oxygen, nitrogen oxide, hydrogen, toluene, and other gases. The sensing material includes at least one of tin oxide foam or tin oxide foam having at least one of palladium, gold, silver, or platinum catalyst in the range of 0.1 weight percent to 3 weight percent.

The sensing material is a metal oxide foam, such as a semiconductor type sensor. The porous sensing material can be any of one or a combination of tin oxide (SnO or SnO2), zinc oxide (ZnO), indium oxide (In2O3), tungsten oxide (WO3), titanium oxide (TiO2), nickel oxide (NiO), copper oxide (CuO), cobalt oxide (Co3O4), chromium oxide (Cr2O3), and iron oxide (Fe2O3), or other metal oxides with similar properties.

A manufacturing process to form the porous metal oxide foam sensing material can includes at least one of freeze casting, space holder, or dealloying, or a combination. A manufacturing process to form the porous metal oxide foam sensing material can includes a freeze casting method followed by a powder slurry preparation and sintering process where water- or camphene-based oxide powder slurry is frozen and dried at low temperature to form a green body and then sintered at high temperature to form a three dimensionally connected solid porous structure.

The sensing material can be a semiconductor type sensor using a metal oxide, and the porous sensing material can be manufactured via at least one of a thermal oxidation or anodizing process on the surface of metal foam (e.g., Sn, Zn, In, W, Ti, Ni, Cu, Co, Cr, or Fe) manufactured via at least one of freeze casting, space holder, or dealloying. The metal oxide sensing material can be constructed in the form of at least one of a thin layer of oxide or nanoneedle oxide on the surface of the prepared metal foam.

The tin oxide foam can be fabricated with addition of a sintering agent in the composition range of about 0.1 weight percent to about 3 weight percent, such as at Li2O, CuO, MnO2, ZnO, or La2O3, or similar, to assist densification by forming a liquid phase during sintering of the tin oxide green body.

In an implementation, a method of creating a metal oxide foam using a freeze casting process includes: placing a rectangular insulated silicone mold on a copper or aluminum block immersed in liquid nitrogen, controlled using a thermocouple and temperature controller, and pouring metal oxide slurry comprising at least one of deionized water, dispersant, binder, metal or metal oxide powder, and a sintering agent into the mold; freezing the slurry, such that ice dendrites form and grow in the slurry and metal or metal oxide particles congregate between the growing ice crystals; forming a green body metal (oxide) foam by drying the ice crystals of the frozen sample at sufficiently low temperature, between about −10 degrees Celsius and about −80 degrees Celsius, and reduced pressure, leaving pores in their original locations; forming three dimensionally connected porous metal oxide foam with substantial integrity by sintering the porous green body at sufficiently high temperature, between about 800 degrees Celsius and about 1700 degrees Celsius, in a controlled furnace under air or argon atmosphere; and machining the metal oxide foam into the form of a rectangle, which can be directly applied as a sensing material in a gas sensor with a ruthenium heater and platinum electrodes beneath it.

In an implementation, a method of applying the fabricated metal oxide foam for a gas sensor includes a patterning process attaching electrode pads to the metal oxide foam sensing material in a suitable pattern. The gas sensor can include a metal-oxide-foam sensing material coupled via silver paste to platinum electrodes and ruthenium heater that are printed on low temperature co-fired ceramic substrate.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIGS. 1A-1C show schematically the general sensing mechanisms for n- and p-type semiconductor sensors.

FIGS. 4A-4H show scanning electron micrographs of radial sections and fracture surfaces for tin oxide foams.

FIG. 12 shows a gas sensor product with a tin oxide foam sensor device, which is used to replace an existing, much larger commercially available sensing module.

DETAILED DESCRIPTION OF THE INVENTION

Figure 2A:
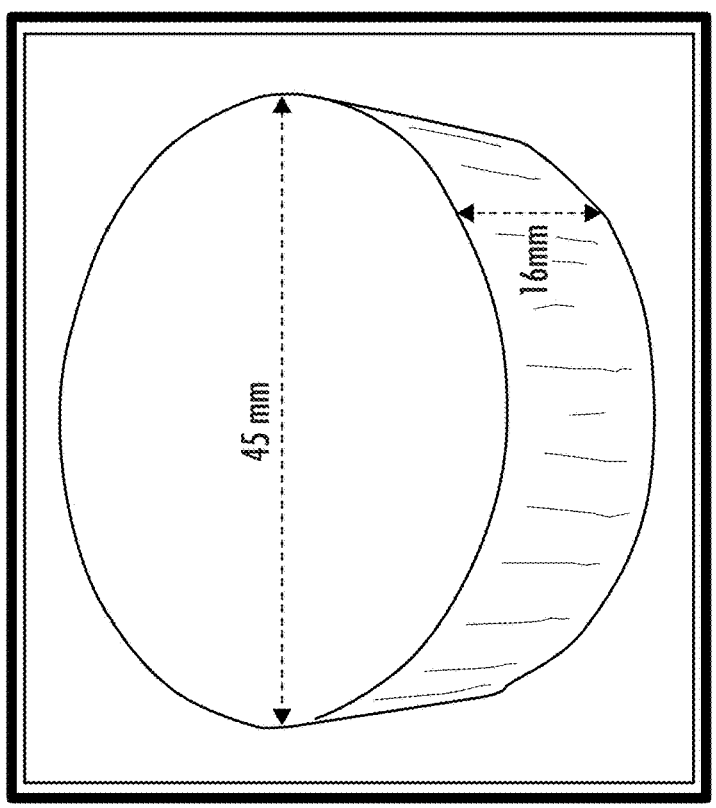
FIG. 2A-2B show photographs of a tin oxide foam sample before and after sintering.

The metal oxide gas sensor is one of the most commonly used sensing devices for commercial gas sensing applications. This sensor is based on the principle of changing electrical resistivity (or conductivity) resulting from gas adsorption on sensing material surface exposed to the target gas.

Common sensing materials are tin oxide (SnO or $SnO_2$) and zinc oxide (ZnO), both of which exhibit excellent semiconductor sensing behavior. Other metal oxide semiconductors, such as copper oxide (CuO), nickel oxide (NiO), titanium oxide ($TiO_2$), tungsten trioxide ($WO_3$), indium oxide ($In_2O_3$), and iron oxide ($Fe_2O_3$) are also being used for new chemical or resistivity functionalities, or a combination, due to their good response and selectivity to ambient conditions, as well as their simplicity of material synthesis and sensing device manufacture.

Controlling the (surface) morphology of the gas sensing material is an effective method to enhance sensing properties. It is important to understand the microstructure of the sensing material, because grain sizes, morphology, surface state, and accessible surface area all play important roles in gas sensing performance. Generally, adsorption or desorption processes occur on the surface of the sensing layer and determine the sensor response.

Therefore, there has recently been a dramatic increase in research development on the design of gas sensing materials, including nanowires, nanoparticles, nanorods, nanotubes, and hollow spheres. However, these efforts have not provided sufficient solutions and the need remains for improved gas sensitivity.

A new gas-sensing device is based on a new metal oxide foam material with an enhanced surface area and higher gas permeability. The three-dimensional pore structure on the surface of the metal oxide foam used in this device can improve the adsorption and desorption processes of the surface sensing layer and thus enhance the sensitivity and response time against the target gas.

Manufacturing the porous structure includes the steps: (a) freezing metal or metal oxide slurry with metal or metal oxide powder and sintering agent powder (e.g., copper oxide) in a silicone mold in contact with the cold surface of a copper rod; (b) sublimating the frozen slurry under reduced pressure and low temperature, forming a porous green body; (c) sintering the porous green body to achieve a three-dimensionally connected porous metal oxide foam; (d) cutting the porous metal oxide foam into 10-millimeter by 20-millimeter panels to be used as sensing material; and (e) patterning the porous foam with platinum electrode pads at 200 micron spacing using a lift-off process and shadow mask.

A porous structure of a tin oxide foam is used as the sensing material of the gas sensor provides higher surface area (e.g., relative to a nonfoam material) with directional channel pores, which can help the target toxic gas flow through. This dual pore structure with large surface area can detect toxic gases when exposed to them with improved sensitivity, such as ethanol, carbon monoxide, and others, as shown schematically in FIG. 1.

A variety of oxide-based gas-sensing semiconductor material foams can be manufactured into three dimensional porous structures, and can all be prepared from the form of starting powders. For example, these foams include tin oxide (SnO or $SnO_2$), zinc oxide (ZnO), indium oxide ($In_2O_3$), tungsten oxide ($WO_3$), titanium oxide ($TiO_2$), nickel oxide (NiO), copper oxide (CuO), cobalt oxide ($Co_3O_4$), chromium oxide ($Cr_2O_3$), and iron oxide ($Fe_2O_3$). The initial material can also be their counterpart metallic powders, since the frozen and dried green bodies composed of the metallic powders may be sintered at high temperature under hydrogen atmosphere for reduction rather than under air atmosphere. Tin oxide and copper foams are a specific example discussed in this patent but other metal oxide materials, as discussed above, can also be applied in the same manner for use as the gas sensing materials, as long as they are also semiconductor materials with a wide band gap, high conductivity, and good stability.

The porous metal oxide foam is a three dimensionally connected porous structure with pore sizes ranging from several hundred nanometers to a few tens of microns, and the pores extending in three dimensions. A three-dimensional metal oxide foam is fabricated based on a combination of slurry foaming and powder sintering. This is a relatively simple, low cost processing method, suitable to fabricate small or large-scale structures. However, the manufacturing process of the porous metal oxide foam is not limited to this powder processing, and other methods can also be utilized to fabricate metal oxide foam structures for application as sensor devices with improved sensitivity.

To manufacture tin oxide foam, a sintering agent, such as copper oxide, may assist with the densification process by forming a sintering liquid phase. A porous tin oxide with a sintering agent (e.g., copper oxide) can achieve uniform volumetric shrinkage of the foam in the sintering process such that cracks do not occur (FIG. 2). We consider the shrinkage to be nearly isotropic, and the residual stress due to shrinkage to be minimal. Tin oxide is well known to be difficult to densify during sintering because the tin oxide mass transport mechanism is rather complex, controlled by surface diffusion at low temperatures (e.g., temperature less than 1000 degrees Celsius) and by evaporative condensation at high temperatures (e.g., temperature greater 1300 degrees Celsius). Uniform densification is difficult to achieve when either of these mechanisms dominates. However, as sintering agent (e.g., copper oxide) has a significant role in promoting bulk or grain-boundary diffusion or forming a liquid phase during sintering of tin oxide, or both.

Based on the described fabrication of tin oxide foam, there can be relatively simple modifications in order to manufacture numerous types of porous metal oxide foams for use as three-dimensional gas sensing material, such as titanium oxide, nickel oxide, cobalt oxide, zinc oxide, and others.

This patent describes some examples of implementations with specific dimensions, measurements, and values. These are not intended to be exhaustive or to limit the invention to the precise form described. The values, percentages, times, and temperatures are approximate values. These values can vary due to, for example, measurement of manufacturing variations or starting powder chemistry or tolerances or other factors. For example, depending on the tightness of the manufacturing and measurement tolerances, the values can vary plus or minus 5 percent, plus or minus 10 percent, plus or minus 15 percent, or plus or minus 20 percent.

Further, the values are for a specific implementation, and other implementations can have different values, such as certain values made larger for a larger-scaled sized process or product, or smaller for a smaller-scaled product. A device, apparatus, or process may be made proportionally larger or smaller by adjusting relative measurements proportionally (e.g., maintaining the same or about the same ratio between different measurements). In various implementations, the values can be the same as the value given, about the same of the value given, at least or greater than the value given, or can be at most or less than the value given, or any combination of these.

A process for manufacturing of porous metal oxide foam for use as gas sensing material can include the following steps:

1. Placing a silicone mold on a copper rod, or similar high thermal conductivity material, immersed in liquid nitrogen and pouring the metal oxide slurry, with powder size being normally in the range of tens or hundreds of nanometers, along with binder and sintering agent(s) in the mold.

2. Freezing the prepared metal oxide slurry where the metal oxide particles are piled up and physically attached between the growing ice crystals.

3. Forming a porous green body by drying the ice crystals from the frozen slurry at sufficiently low temperature and reduced pressure, leaving pores in the structure and retaining the physical attachments.

4. Solidifying metal oxide foam with firmly connected pores by de-binding and sintering the porous green body at sufficiently high temperature under air atmosphere.

5. Cutting the porous metal oxide foam into the form of a 10-millimeter by 20-millimeter rectangles to employ as sensing material in the gas sensor.

6. Patterning the porous foam with two platinum electrode pads at 200 micron spacing by a lift-off process using a shadow mask.

Exemplary Embodiment 1: Preparing Tin Oxide Foam

Tin oxide powder (e.g., 15.5 grams) was suspended in a 20-milliliter solution of deionized water containing polyvinyl alcohol binder, and a sintering agent (e.g., copper oxide (CuO) powder, less than 3 weight percent) was added to improve the tin oxide powder densification. The slurry was dispersed using a manual stirrer for 30 minutes and then sonicated for 1 hour. To ensure sufficient particle dispersion, the stirring process was repeated twice.

The slurry was then cooled to a few degrees above the freezing point of water and poured into a cylindrical mold consisting of insulated polytetrafluoroethylene (PTFE), Teflon, or silicone, or a combination, on a copper rod. The copper rod was cooled using liquid nitrogen controlled by a thermocouple and temperature controller.

Once the freezing process was complete, the frozen tin oxide green-body foam sample was removed from the mold and dried at −80 degrees Celsius for 48 hours in a freeze dryer under $10^{-2}$ torr residual pressure and subsequently heat treated in two separate steps. The first treatment was 300 degrees Celsius for 3 hours to remove the binder, followed by sintering at 1150 degrees Celsius in a box furnace in atmospheric air for 10 hours.

Exemplary Embodiment 2: Preparing a Sensing Device

To manufacture a highly sensitive gas-sensing device, two platinum electrode pads and a ruthenium oxide heater were printed on low temperature co-fired ceramic (LTCC) substrate. With via punching and silver (Ag) paste filling, a ruthenium oxide ($RuO_2$) heater layer was created, followed by the patterning of two platinum electrodes at 200-micron gap using a lift-off process and shadow mask. Gas sensitivity was then measured at different ethanol gas concentrations from 20-60 parts per million at 300 degrees Celsius. For carbon monoxide gas detection performance, sensor response was measured for low concentrations of 100-500 parts per million and high concentrations of 1000-5000 parts per million at 200-300 degrees Celsius. During the measurements, gas concentrations were balanced and controlled by a mass flow controller (MFC), with gas being injected into the sensor chamber while continuously measuring the sensor electrical resistance at constant microangstroms.

FIGS. 1A-1C show schematically the general sensing mechanisms for n- and p-type semiconductor sensors and in particular the sensing mechanism for the example tin oxide foam sensor presented in this patent.

Figure 2B:
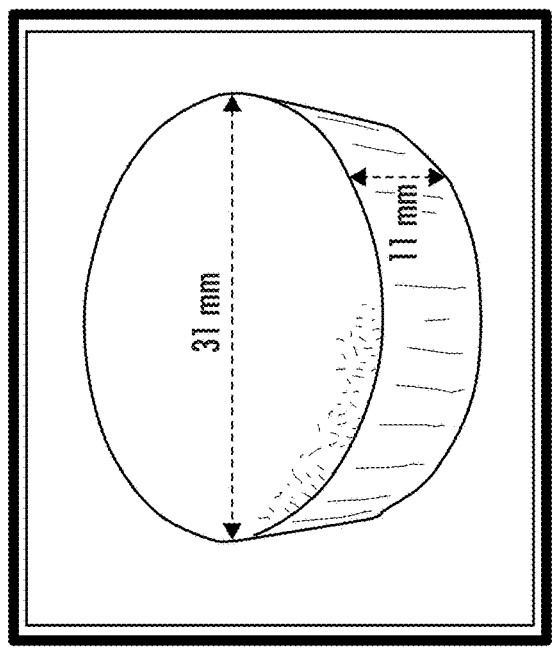

FIGS. 2A-2B show photographs of a representative tin oxide foam before and after sintering in air. The foam reduced from 45-millimeter diameter and 16-millimeter height (FIG. 2A, left) to 31-millimeter diameter and 11-millimeter height (FIG. 2B, right), resulting in a 67 percent volumetric shrinkage, with approximately equal 31 percent radial and height shrinkages. The sample maintains its integrity after sintering without cracking or warping. Therefore, the shrinkage is considered to be nearly isotropic, which suggests minimal residual stress due to shrinkage.

Figure 3A:
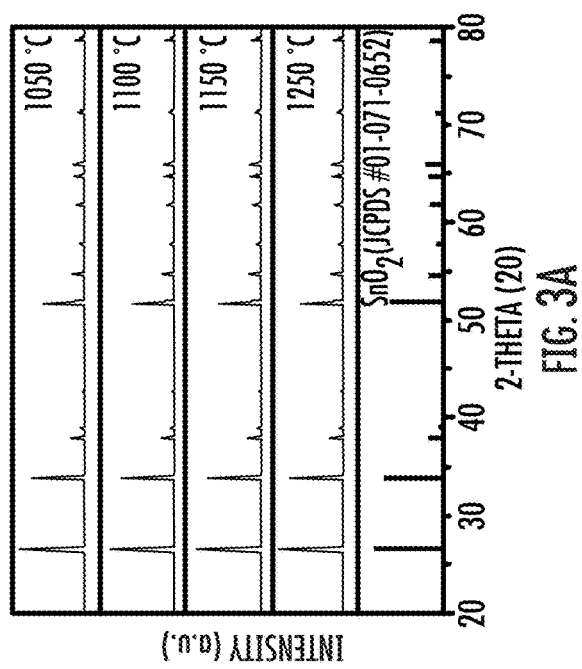
FIG. 3A shows X-ray diffraction patterns for tin oxide foam samples heat treated at various temperatures.

FIG. 3A shows X-ray diffraction patterns of four tin oxide foam samples heat treated at 1050 degrees Celsius, 1100 degrees Celsius, 1150 degrees Celsius, and 1250 degrees Celsius, respectively, for 10 hours. There was no significant difference between the X-ray diffraction (XRD) peaks of the four foam samples, and they all show typical tin oxide ($SnO_2$) peaks.

Figure 3B:
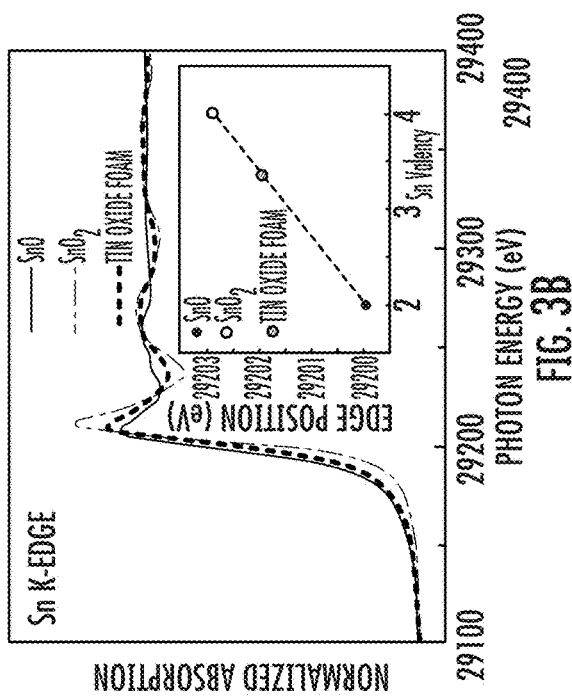
FIG. 3B shows tin K-edge X-ray absorption near edge structure spectra for tin oxide foam.

FIG. 3B shows tin K-edge x-ray absorption near edge structure spectra for tin oxide foam heat treated at 1150 degrees Celsius for 10 hours compared with commercially obtained tin monoxide (SnO) and tin dioxide ($SnO_2$) powders; and three-dimensional X-ray photoelectron spectroscopy spectra of (FIG. 3C) survey and (FIG. 3D) three-dimensional metallic tin of tin oxide foam after sintering in air at 1150 degrees Celsius for 10 hours.

The oxidation state of tin in the foam was characterized by obtaining the tin (Sn) K-edge XANES spectra (FIG. 3B), and comparing the absorption edge position of the foam with and those of commercial tin oxide (e.g., SnO and $SnO_2$) powders. Average tin valency is 3.36 in the foam sample, suggesting that tin oxidation state in the entire foam sample is predominantly tin dioxide ($SnO_2$).

Figure 3C:
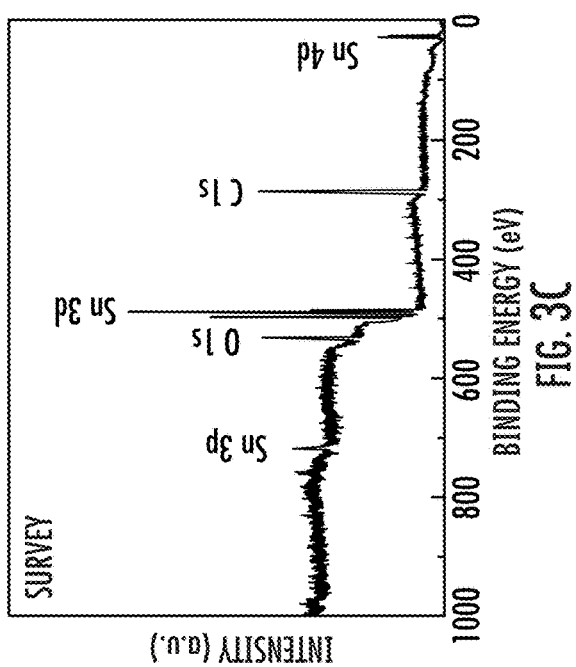
FIG. 3C shows X-ray photoelectron spectroscopy measurements for tin oxide.
Figure 3D:
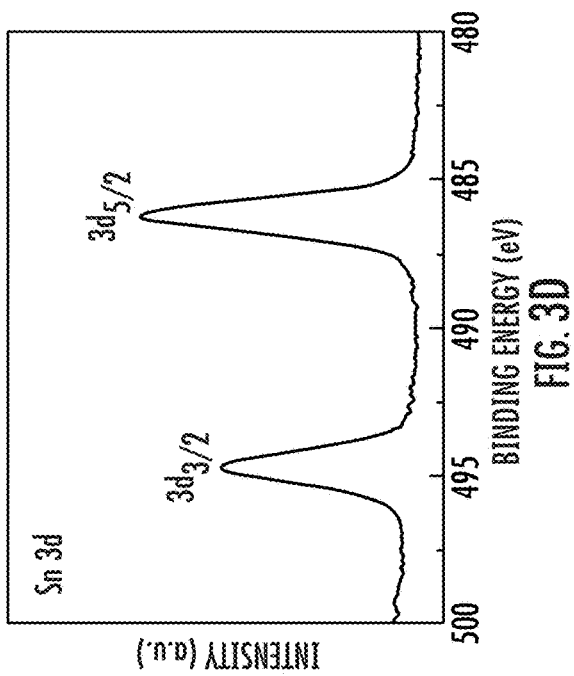
FIG. 3D shows the binding energy positions for tin oxide.
Figure 4D:
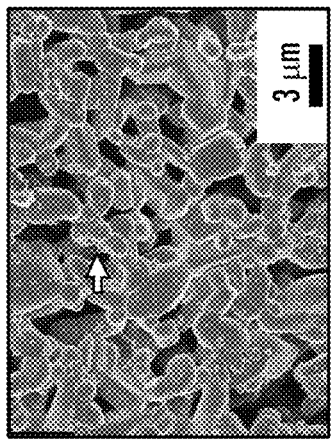
Figure 4H:
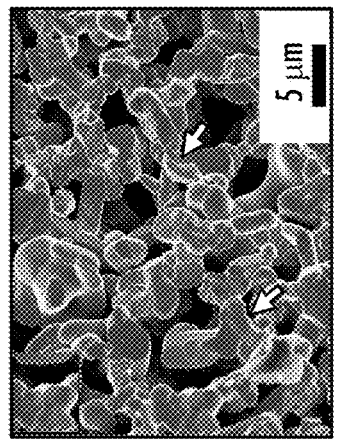
Figure 4C:
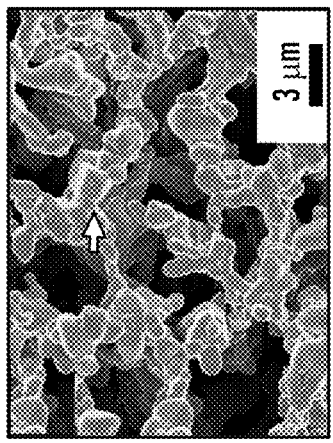
Figure 4G:
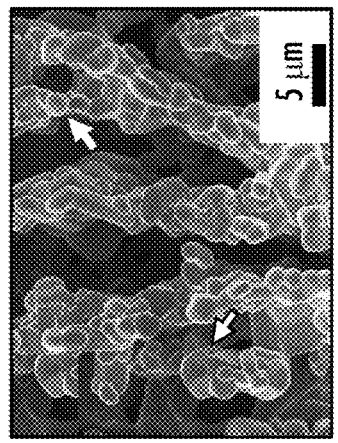
Figure 4A:
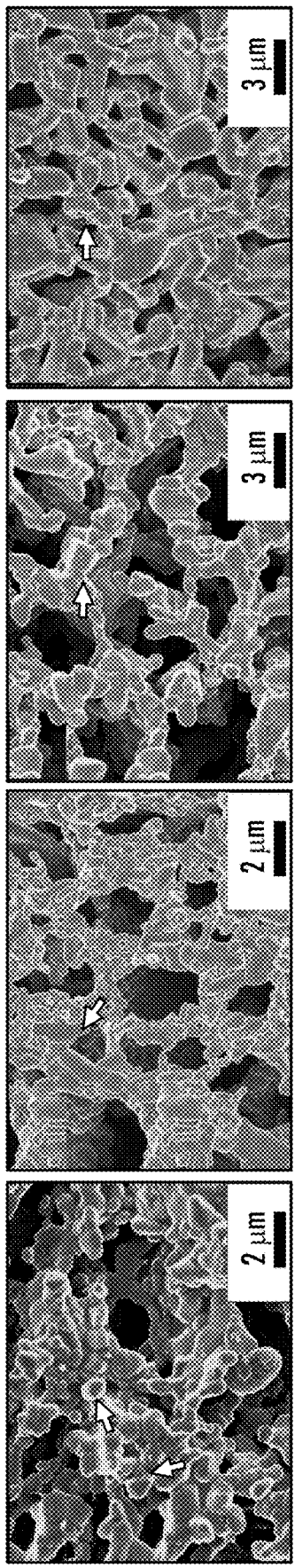
Figure 4E:
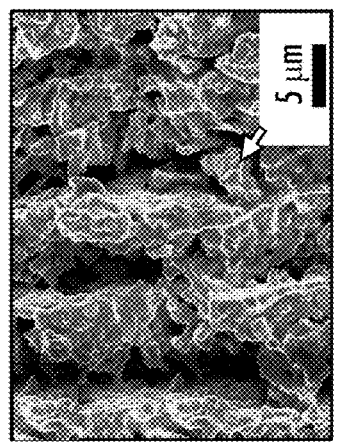

FIG. 3C shows X-ray photoelectron spectroscopy (XPS) measurements, taken to investigate the chemical state of the tin oxide foam surfaces. FIG. 3D shows the binding energy positions of the tin 3d peaks (486.3 electron volts for $3d_{5/2}$ and 494.7 electron volts for $3d_{3/2}$) verify that the foam surfaces are also composed of tin oxide (SnO).

FIGS. 4A-4H show scanning electron micrographs of radial sections and fracture surfaces for tin oxide foams sintered at various temperatures, resulting in a dual pore structure: (FIGS. 4A and 4E) 1050 degrees Celsius, (FIGS. 4B and 4F) 1100 degrees Celsius, (FIGS. 4C and 4G) 1150 degrees Celsius, and (FIGS. 4D and 4H) 1250 degrees Celsius for 10 hours. Arrows in the top view images (e.g., FIGS. 4A-4D) indicate junctions typical of metal oxide powder sintering processes and the arrows in the fracture surface (e.g., FIGS. 4E-4H) indicate secondary dendrites on the wall struts.

Figure 5A:
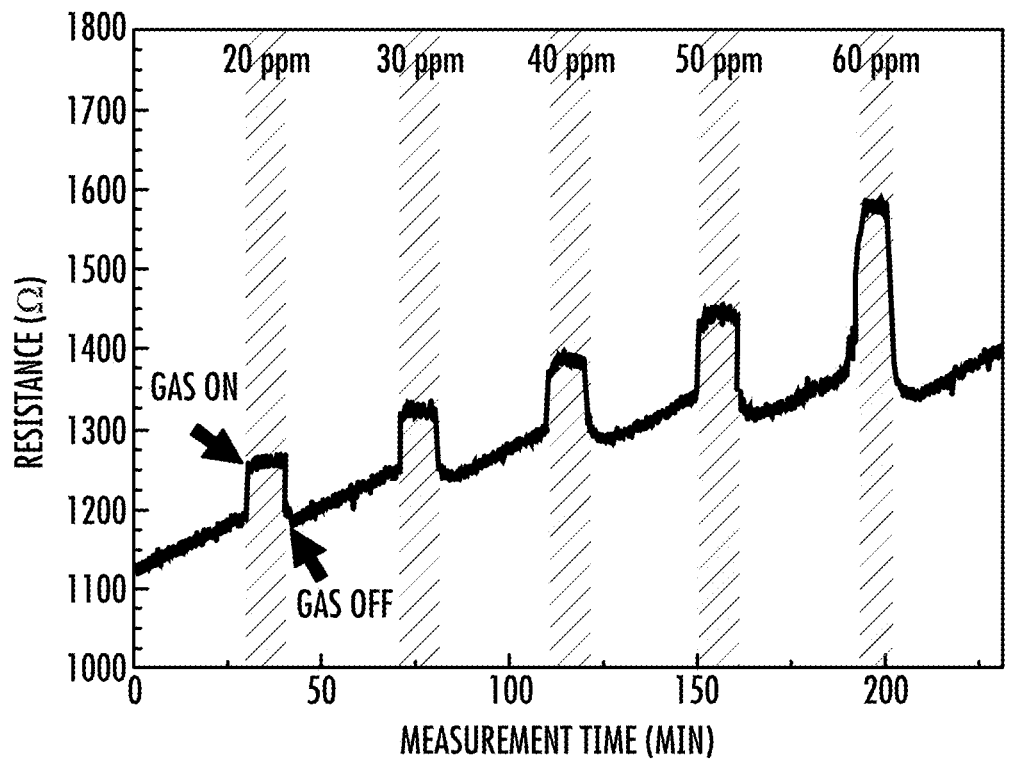
FIGS. 5A-5B show variation in the electrical resistance (gas sensitivity) of tin oxide foam for different exposure times to various concentrations of ethanol (FIG. 5A) and carbon monoxide gases (FIG. 5B).
Figure 5B:
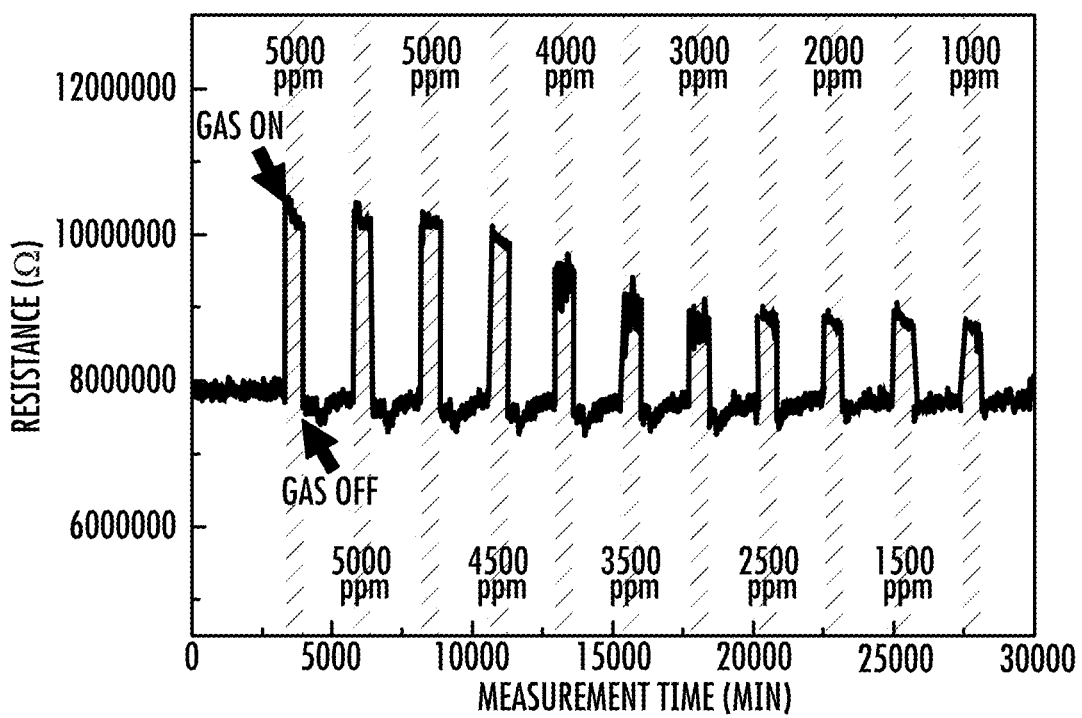

FIGS. 5A-5B show variation in the electrical resistance (gas sensitivity) of tin oxide foam heat treated at 1150 degrees Celsius for 10 hours, for different exposure times to various concentrations of (FIG. 5A) ethanol and (FIG. 5B) carbon monoxide gas. The electrical resistance variations confirm that the tin oxide foam sample would operate remarkably in a gas-sensing device.

FIG. 5A shows the resistance variation or sensitivity of a tin oxide foam sample with respect to measurement time during exposure to ethanol gas with concentrations from 20-60 parts per million. The tin oxide foam responded with a substantial increase in electrical resistance with increased exposure to ethanol gas (e.g., FIG. 5A, striped columns), and the resistance returned to stable values when the gas was substituted by pure air (e.g., FIG. 5A, white columns). The tin oxide foam showed a response of 13.1 (no unit) for 60 parts per million ethanol gas at 300 degrees Celsius, which is quite remarkable given that no catalyst was added. Thus, tin oxide foam synthesized the method embodied in this patent is suitable as an ethanol gas sensing material.

FIG. 5B shows the resistance variation or sensitivity of a tin oxide foam with respect to measurement time during exposure to carbon monoxide gas with concentrations from 1000-5000 parts per million. The tin oxide foam sensor showed a response value of 35.9 (no unit) at 5000 parts per million monoxide gas at 200 degrees Celsius with no added catalyst. The sensitivity increased almost linearly with increasing monoxide concentration. Thus, tin oxide foam synthesized the method embodied in this patent is suitable as a carbon monoxide gas sensing material.

Figure 6A:
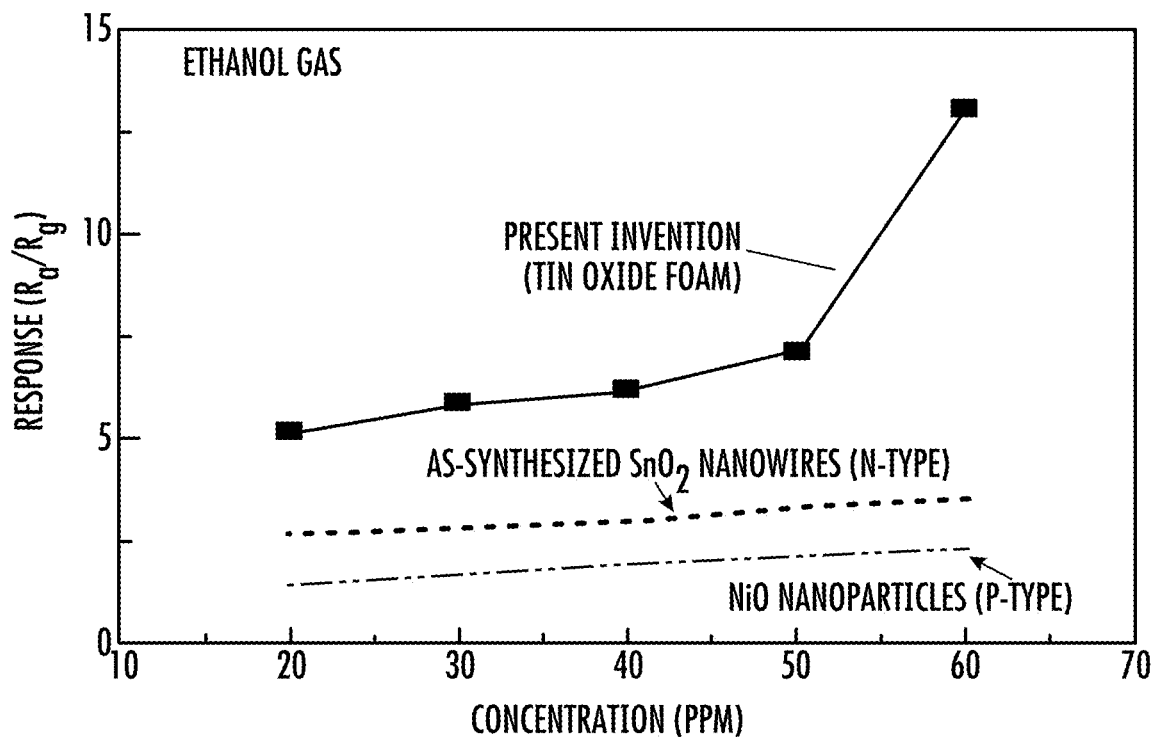
FIGS. 6A-6B compares sensing responses for tin oxide foam in ethanol and carbon monoxide gases.
Figure 6B:
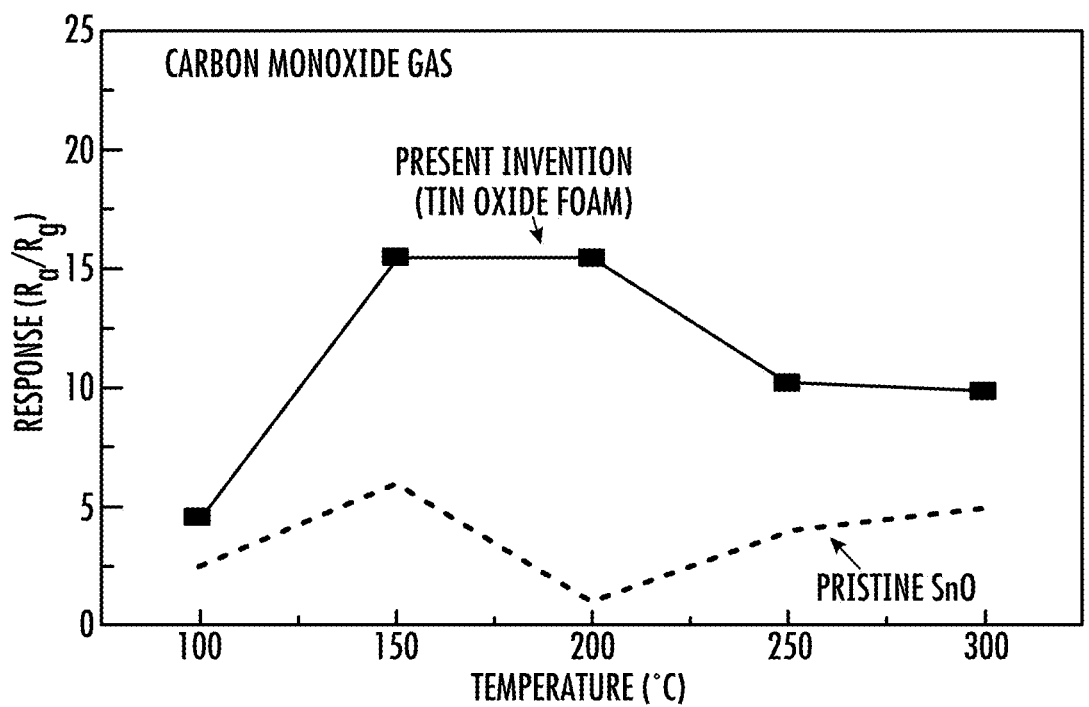

FIGS. 6A-6B compares sensing responses for tin oxide foam with those of (FIG. 6A) NiO nanoparticles and tin oxide $SnO_2$ nanowires as a function of ethanol concentration at 300 degrees Celsius and (FIG. 6B) tin oxide thin film samples at various temperatures under carbon monoxide gas. The tin oxide foam sample successfully detects carbon monoxide gas at substantially lower concentration than conventional tin oxide thin film.

The three-dimensional tin oxide foam sensing material fabricated as detailed in examples 1 and 2 achieved higher sensitivity compared to other sensing materials without requiring additional catalysts, as shown in FIG. 6A. In particular, FIG. 6B shows that the three-dimensional tin oxide foam fabricated as detailed in this patent detected carbon monoxide gas at very lower concentrations, which could not be achieved by conventional tin oxide thin films. Thus, is due to the unique three-dimensional porous tin oxide structure enabling easy diffusion of toxic gases through the channel-like pores, and increased surface area by adjusting major processing parameters, such as sintering conditions and powder content. Thus, the tuned pore structure in the tin oxide foam facilitates gas diffusion by shortening the reaction path.

Figure 7A:
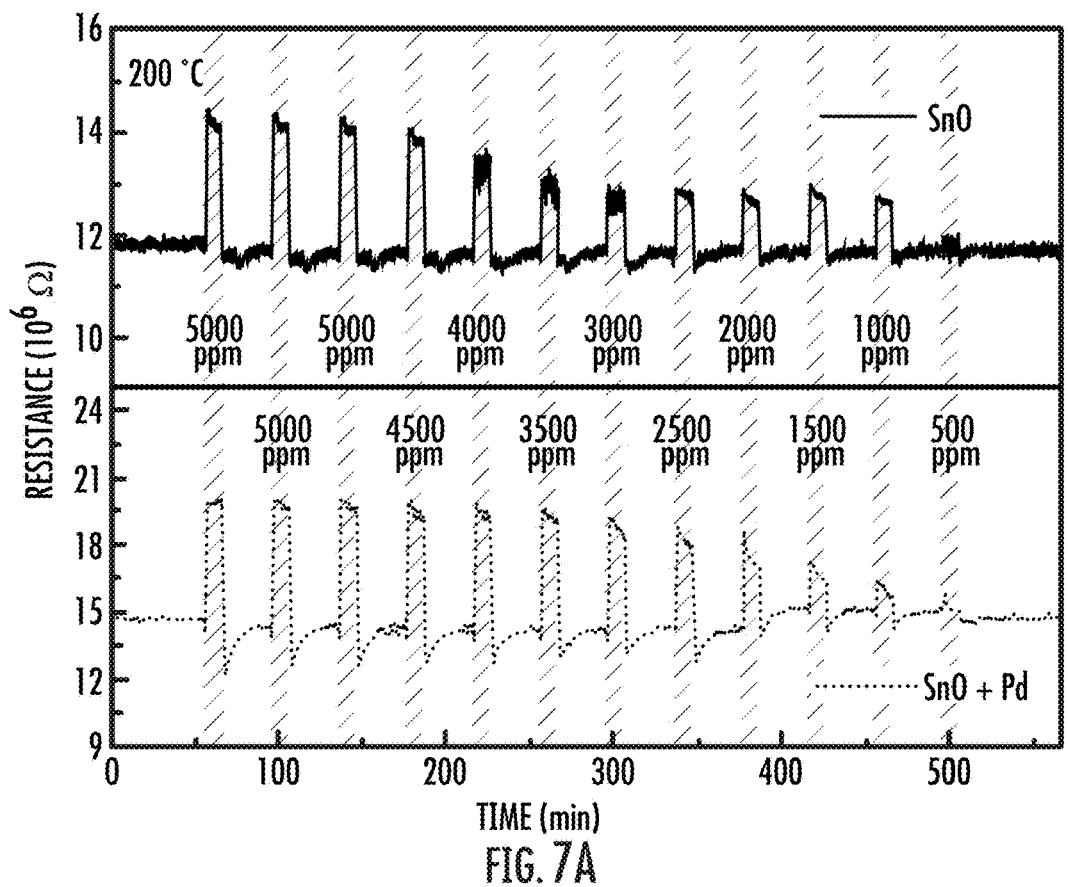
FIGS. 7A-7B compares variations in electrical resistance and gas sensitivity of tin oxide foams with and without the addition of palladium at 200 degrees Celsius.
Figure 7B:
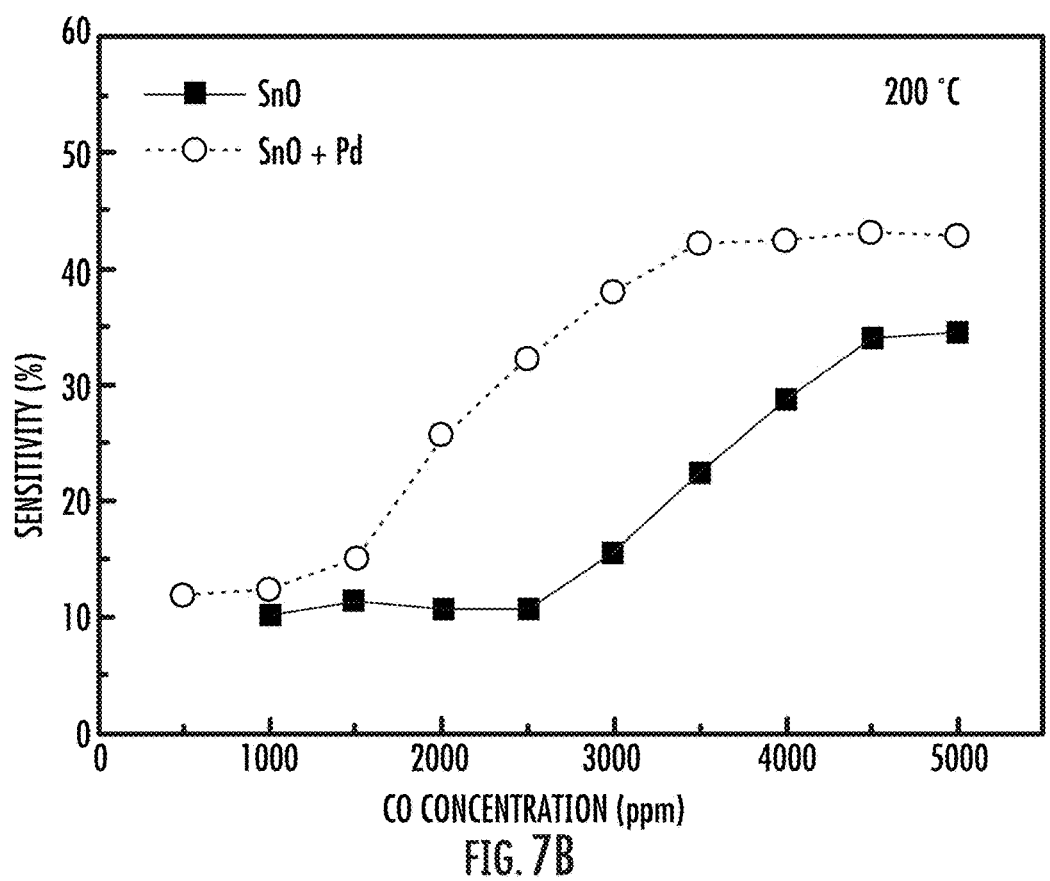

FIGS. 7A-7B show (FIG. 7A) variations in electrical resistance (gas sensitivity) of tin oxide foam with the addition of 3.0 weight percent palladium as a catalyst for various carbon monoxide gas concentrations in comparison with those of tin oxide foam without the addition of palladium and (FIG. 7B) the sensitivity comparison between the tin oxide foams with and without the addition of palladium as a function of carbon monoxide gas concentration at 200 degrees Celsius.

A small addition of catalyst such as palladium, platinum, or other can certainly improve the sensitivity of the metal oxide foam sensor. FIG. 7A shows comparison in electrical resistance variations (gas sensitivity) of tin oxide foams with and without the addition of 3.0 weight percent palladium as a catalyst for various carbon monoxide gas concentrations. As shown in FIG. 7B, the sensitivity of the tin oxide foam sensor with the addition of palladium is considerably higher in the entire range of carbon monoxide gas concentrations at 200 degrees Celsius than that of the tin oxide foam sensor without palladium. Furthermore, the sensitivity of the tin oxide foam sensor containing palladium is higher in the entire temperature range of from 200 degrees Celsius to 300 degrees Celsius than that of the tin oxide foam sensor without palladium (FIG. 8).

Figure 8:
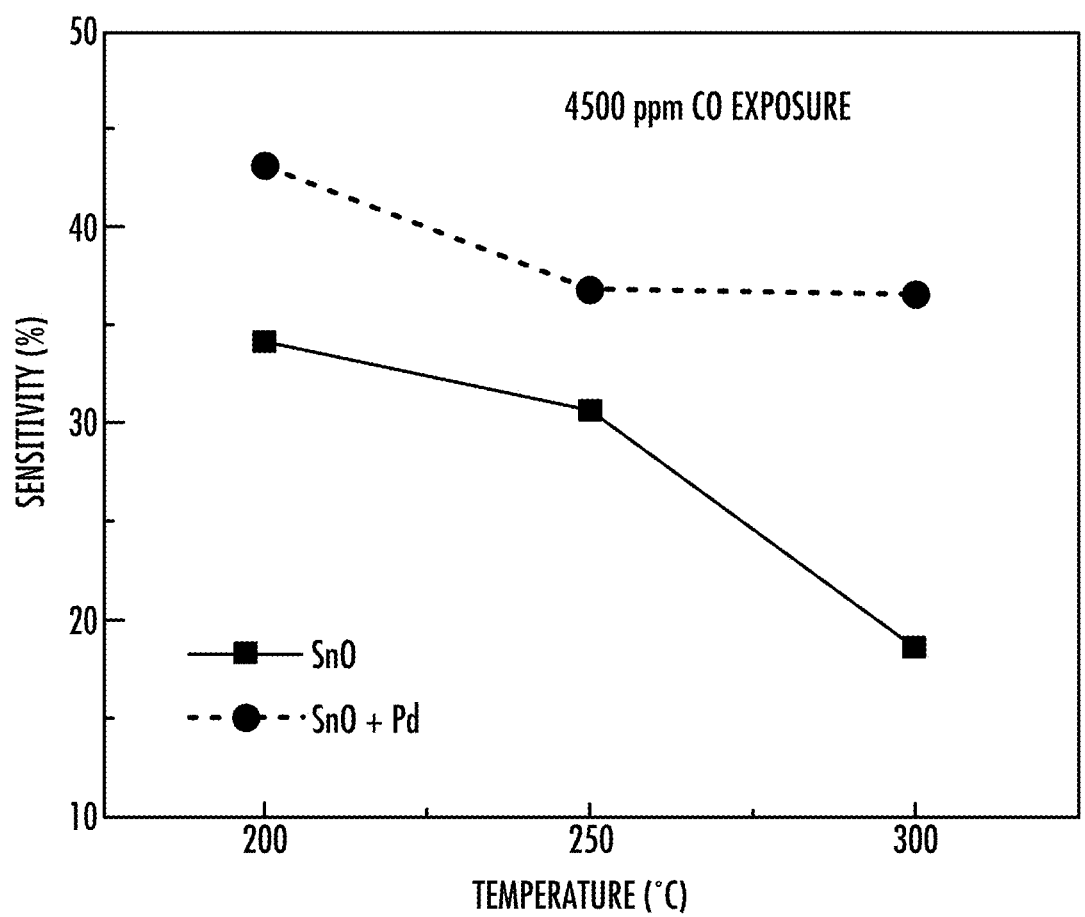
FIG. 8 shows a sensitivity comparison between the tin oxide foams with and without the addition of palladium at various temperatures.

FIG. 8 shows the sensitivity comparison between the tin oxide foams with and without the addition of palladium at various temperatures at 4500 parts per million (ppm) carbon monoxide gas concentration. The tin oxide foam with the addition of palladium exhibits considerably higher sensitivity at all temperature ranges between 200 and 300 degrees Celsius.

Figure 9A:
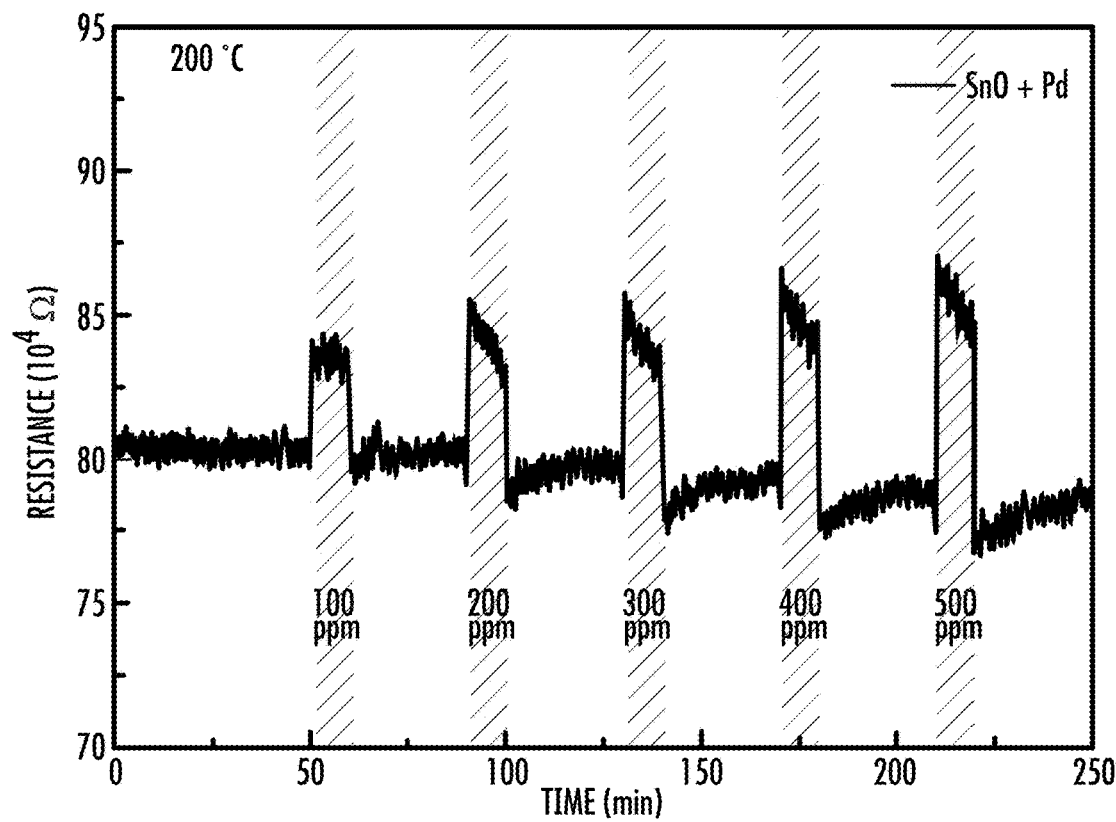
FIGS. 9A-9B show variation in electrical resistance and gas sensitivity of tin oxide foam with the addition of palladium as a catalyst at low concentrations and 200 degrees Celsius.
Figure 9B:
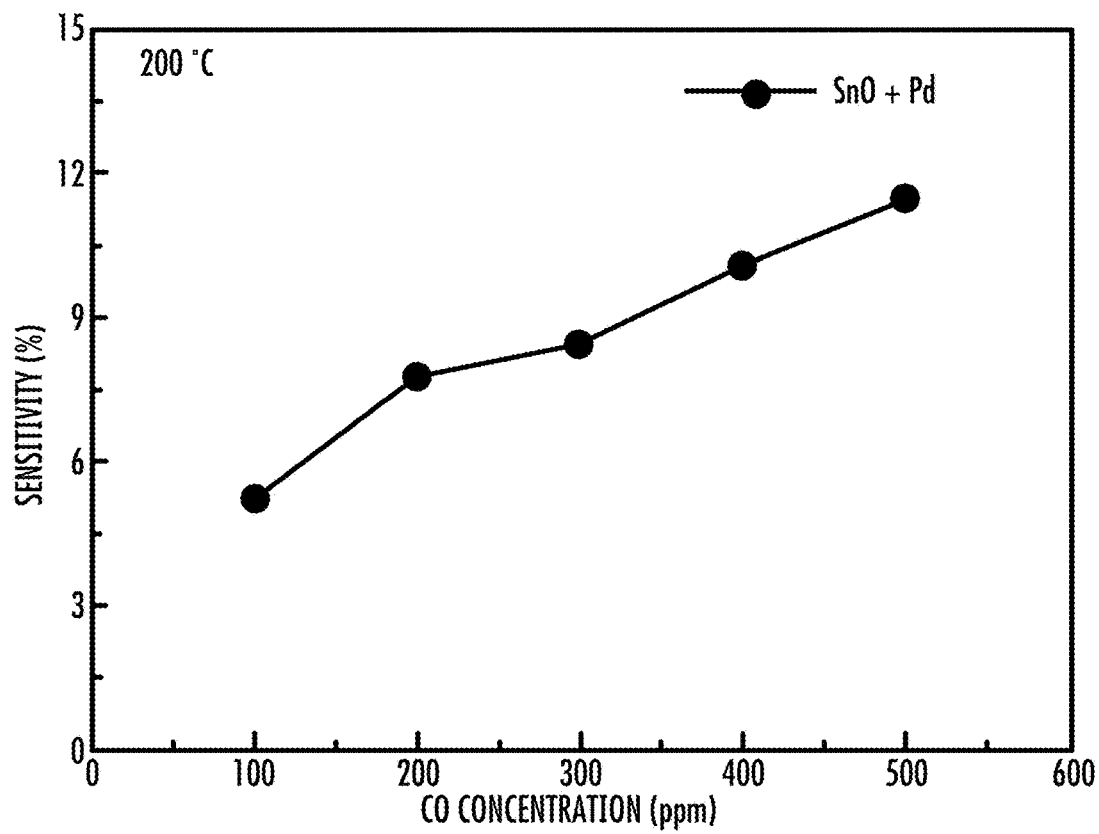

FIGS. 9A-9B show (FIG. 9A) variation in electrical resistance (gas sensitivity) of tin oxide foam with the addition of palladium as a catalyst at low concentrations (from 100 to 500 ppm) of carbon monoxide gas at 200 degrees Celsius and (FIG. 9B) the sensitivity of tin oxide foam with the addition of palladium as a function of carbon monoxide gas concentration between 100 and 500 parts per million (ppm) at 200 degrees Celsius.

In particular, the addition of palladium is beneficial for a low concentration range of carbon monoxide gas. FIG. 9A shows variation in electrical resistance (gas sensitivity) of tin oxide foam with the addition of palladium as a catalyst at low concentrations (e.g., from 100 to 500 parts per million) of carbon monoxide gas at 200 degrees Celsius. In such low concentration range of carbon monoxide gas, the sensitivity of tin oxide foam with the addition of palladium steadily increases with increasing carbon monoxide gas concentration between 100 and 500 parts per million at 200 degrees Celsius.

Figure 10A:
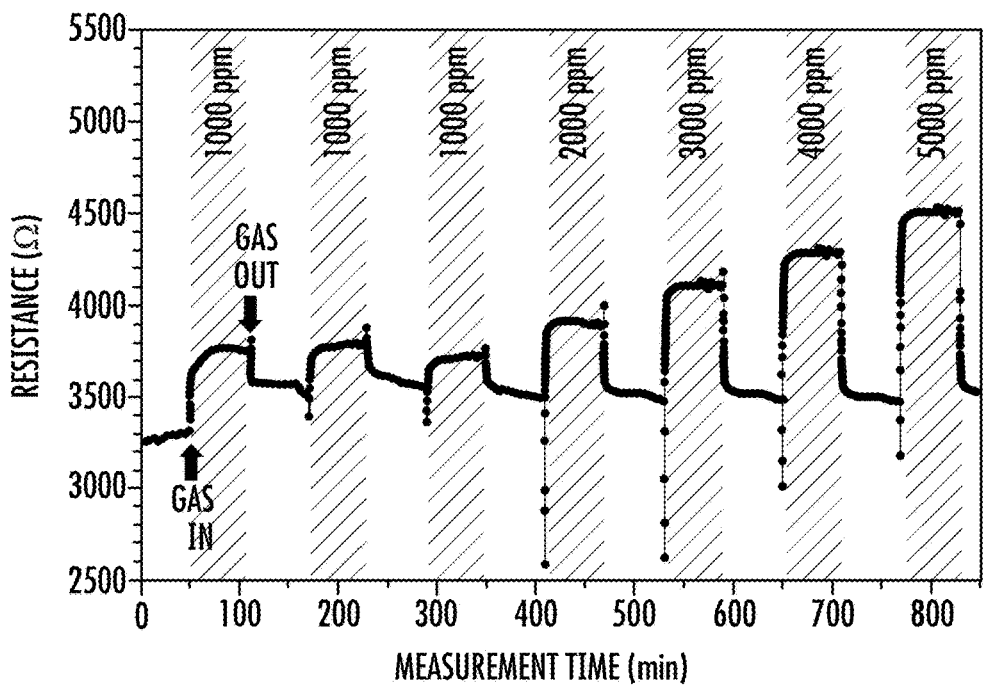
FIGS. 10A-10C show variation in electrical resistance and gas sensing mechanism, and sensing response of copper oxide foam under various carbon monoxide concentrations.
Figure 10B:
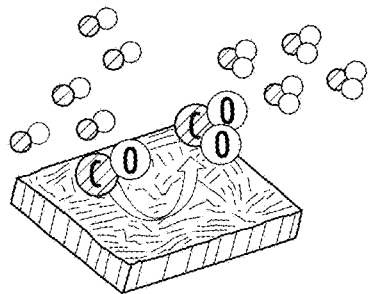
Figure 10B:
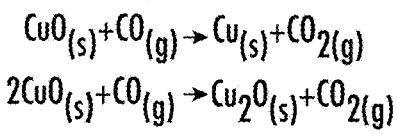
Figure 10C:
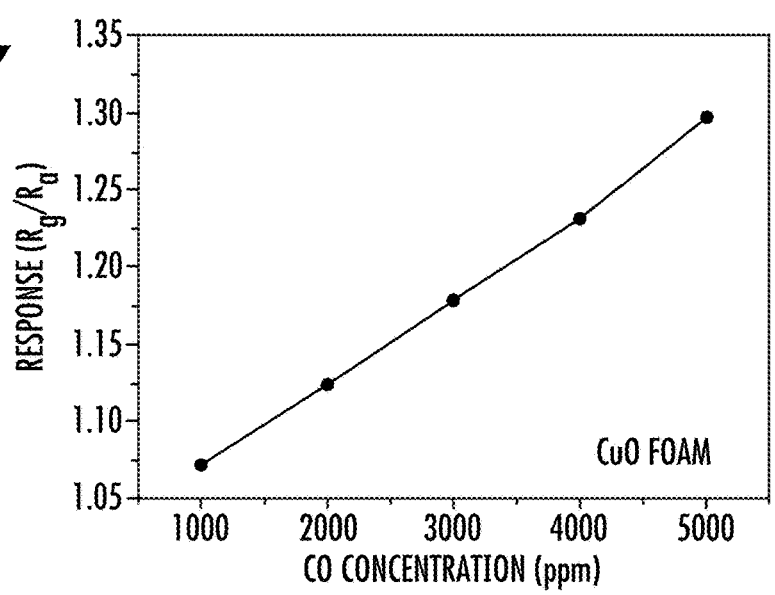
Figure 11A:
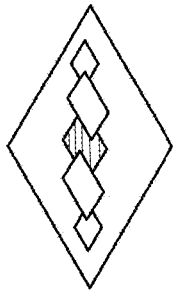
FIGS. 11A-11G show a schematic processing flow of manufacturing metal oxide foam gas sensor device where platinum electrodes and ruthenium oxide heater are printed on LTCC substrate.
Figure 11B:
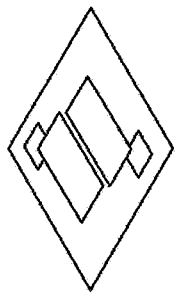
Figure 11C:
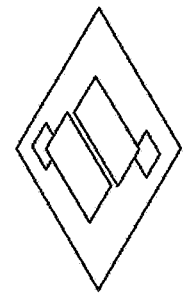
Figure 11D:
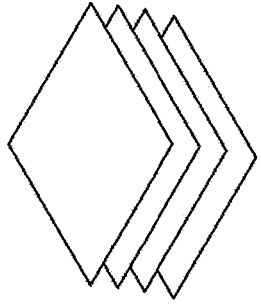
Figure 11E:
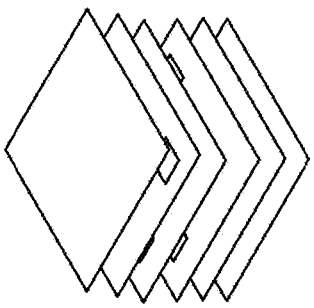
Figure 11F:
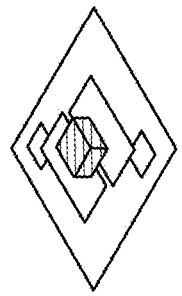
Figure 11G:
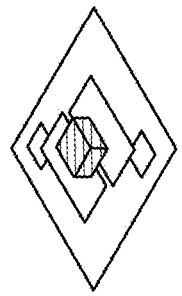

FIGS. 10A-10C show (FIG. 10A) variation in electrical resistance (gas sensitivity) of copper oxide foam at carbon monoxide concentration of from 1000 parts per million (ppm) to 5000 parts per million at 300 degrees Celsius with (FIG. 10B) schematic of its operating mechanism and (FIG. 10C) the sensitivity (response) of copper oxide foam as a function of carbon monoxide gas concentration between 1000 and 5000 parts per million at 300 degrees Celsius.

For the manufacture of metal foam oxide gas sensing device, not only is the tin oxide foam sensor applicable, but other metal oxide foam sensors can also be applied. FIG. 10A shows variation in electrical resistance (gas sensitivity) of freeze-cast copper oxide foam at relatively low carbon monoxide concentrations of from 1000 parts per million to 5000 parts per million at 300 degrees Celsius and FIG. 10C exhibits steadily increasing sensitivity of copper oxide foam with increasing carbon monoxide gas concentration between 1000 and 5000 parts per million at 300 degrees Celsius, confirming the metal oxide sensor structure is beneficial for detecting toxic gases such as carbon monoxide with its enhanced sensing surface area. Here, the copper oxide foam was fabricated using freeze casting. Copper oxide powder was mixed with polyvinyl alcohol in deionized water using stirring and sonication. The dispersed suspension was poured into a silicone mold on the chilled Cu rod where the temperature was fixed at −10 degrees Celsius using liquid nitrogen and a heater. After the suspension was completely frozen, the frozen sample was sublimated at −88 degrees Celsius in vacuum for 40 hours in a dryer. The green body was then reduced from cupric oxide (CuO) to copper in a hydrogen atmosphere before sintering. The reduction and sintering processes were carried out with pre-sintering at 250 degrees Celsius for 4 hours and high-temperature sintering at 800 degrees Celsius for 14 hours in a tube furnace under hydrogen mixture gas.

FIGS. 11A-11G show a schematic processing flow of manufacturing metal oxide foam gas sensor device where platinum electrodes and ruthenium oxide heater are printed on low temperature co-fired ceramic (LTCC) substrate prior to the metal oxide foam sensor attachment on top of the heater and electrodes using silver paste.

An example of manufacturing metal oxide sensor electrode device is described in FIG. 11A-11G, which shows schematic processing flow of manufacturing metal oxide foam gas sensor electrode device where platinum electrodes and ruthenium oxide heater are printed on LTCC substrate prior to attaching the metal oxide foam sensor in contact with the heater and electrodes using silver paste. This sensor device is significantly smaller than, for example, a commercially available sensing module 1203 shown in FIG. 12, and can directly replace the existing sensing material component.

FIG. 12 shows a tin oxide foam sensor device 1212 manufactured as described in this patent that can directly replace the existing sensing module in a commercially available gas sensor product (e.g., carbon monoxide sensor product).

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A gas sensor device comprising:
    a metal-oxide-foam sensing material coupled via silver paste to platinum electrodes and ruthenium heater that are printed on low temperature co-fired ceramic substrate,
    where an electrode pattern includes two electrode pads of a suitable metal, comprising platinum, with spacing of a few hundred micrometers using a lift-off process and shadow mask for use as the electrodes of the attached metal oxide foam sensor.

2. The device of claim 1 where the metal oxide foam has a porosity between about 55 percent and about 90 percent and is a semiconductor-type gas sensing material in a sensor device, which reacts with a specific target gas, comprising at least one of ethanol, carbon monoxide, oxygen, nitrogen oxide, hydrogen, or toluene.

3. The device of claim 2 where the semiconductor-type gas sensing material comprises at least one of tin oxide foam or tin oxide foam comprising at least one of gold, silver, or platinum catalyst in the range of 0.1 weight percent to 3 weight percent.

4. The device of claim 3 wherein the tin oxide foam is fabricated with addition of a sintering agent in the composition range of about 0.1 weight percent to about 3 weight percent, comprising at least one of $Li_2O$, CuO, $MnO_2$, ZnO, or $La_2O_3$—to assist densification by forming a liquid phase during sintering of the tin oxide green body.

5. The device of claim 2 where the semiconductor-type gas sensing material is a metal oxide foam, comprising a semiconductor-type sensor.

6. The device of claim 5 where the semiconductor-type gas sensing material can be any of one or a combination of tin oxide (SnO or $SnO_2$), zinc oxide (ZnO), indium oxide ($In_2O_3$), tungsten oxide ($WO_3$), titanium oxide ($TiO_2$), nickel oxide (NiO), copper oxide (CuO), cobalt oxide ($Co_3O_4$), chromium oxide ($Cr_2O_3$), and iron oxide ($Fe_2O_3$).

7. The device of claim 2 where a manufacturing process to form the porous metal oxide foam sensing material comprises at least one of freeze casting, space holder, or dealloying.

8. The device of claim 2 where a manufacturing process to form the porous metal oxide foam sensing material comprises a freeze casting method followed by a powder slurry preparation and sintering process where water- or camphene-based oxide powder slurry is frozen and dried at low temperature to form a green body and then sintered at high temperature to form a three dimensionally connected solid porous structure.

9. The device of claim 1 wherein a manufacturing process to form the gas sensor device comprises:
    placing a rectangular insulated silicone mold on a copper or aluminum block immersed in liquid nitrogen, controlled using a thermocouple and temperature controller, and pouring metal oxide slurry comprising at least one of deionized water, dispersant, binder, metal or metal oxide powder, and a sintering agent into the mold;
    freezing the slurry, such that ice dendrites form and grow in the slurry and metal oxide particles congregate between the growing ice crystals;
    forming a green-body metal oxide foam by drying the ice crystals of the frozen sample at sufficiently low temperature, between about -10 degrees Celsius and about -80 degrees Celsius, and reduced pressure, leaving pores in their original locations;
    forming three dimensionally connected porous metal oxide foam with substantial integrity by sintering the porous green body at sufficiently high temperature, between about 800 degrees Celsius and about 1700 degrees Celsius, in a controlled furnace under air or argon atmosphere; and
    machining the metal oxide foam into the form of a rectangle or circular shape, which can be directly applied as a sensing material in the gas sensor device with a ruthenium heater and platinum electrodes beneath it.

10. The gas sensor device of claim 1 wherein the metal-oxide-foam comprises a copper oxide (CuO) foam.

11. The device of claim 10 where the metal oxide foam has a porosity between about 55 percent and about 90 percent and is a semiconductor-type gas sensing material in a sensor device, which reacts with a specific target gas, comprising at least one of ethanol, carbon monoxide, oxygen, nitrogen oxide, hydrogen, or toluene.

12. The device of claim 11 where the semiconductor-type gas sensing material comprises at least one of tin oxide foam or tin oxide foam comprising at least one of palladium, gold, silver, or platinum catalyst in the range of 0.1 weight percent to 3 weight percent.

13. The device of claim 11 where the semiconductor-type gas sensing material is a metal oxide foam, comprising a semiconductor-type sensor.

14. The device of claim 13 where the semiconductor-type gas sensing material can be any of one or a combination of tin oxide (SnO or $SnO_2$), zinc oxide (ZnO), indium oxide ($In_2O_3$), tungsten oxide ($WO_3$), titanium oxide ($TiO_2$), nickel oxide (NiO), copper oxide (CuO), cobalt oxide ($Co_3O_4$), chromium oxide ($Cr_2O_3$), and iron oxide ($Fe_2O_3$).

15. The device of claim 11 where a manufacturing process to form the porous metal oxide foam sensing material comprises at least one of freeze casting, space holder, or dealloying.

16. The device of claim 11 where a manufacturing process to form the porous metal oxide foam sensing material comprises a freeze casting method followed by a powder slurry preparation and sintering process where water- or camphene-based oxide powder slurry is frozen and dried at low temperature to form a green body and then sintered at high temperature to form a three dimensionally connected solid porous structure.

17. The gas sensor device of claim 1 wherein the metal-oxide-foam comprises a tin oxide ($SnO_2$) foam.

18. The gas sensor device of claim 1 wherein the metal-oxide-foam comprises a tin oxide ($SnO_2$) foam, and
    the metal oxide foam has a porosity between about 55 percent and about 90 percent and is a semiconductor-type gas sensing material in a sensor device, which reacts with a specific target gas, comprising at least one of ethanol, carbon monoxide, oxygen, nitrogen oxide, hydrogen, or toluene.

19. A gas sensor device comprising:
   a metal-oxide-foam sensing material coupled via silver paste to platinum electrodes and ruthenium heater that are printed on low temperature co-fired ceramic substrate,
   where the metal oxide foam has a porosity between about 55 percent and about 90 percent and is a semiconductor-type gas sensing material in a sensor device, which reacts with a specific target gas, comprising at least one of ethanol, carbon monoxide, oxygen, nitrogen oxide, hydrogen, or toluene,
   where the semiconductor-type gas sensing material is a semiconductor-type sensor using a metal oxide, and the semiconductor-type gas sensing foam material is manufactured via at least one of a thermal oxidation or anodizing process on the surface of metal foam, comprising at least one of Sn, Zn, In, W, Ti, Ni, Cu, Co, Cr, or Fe, manufactured via at least one of freeze casting, space holder, or dealloying.

20. The device of claim 19 where the metal oxide sensing foam material is constructed in the form of at least one of a thin layer of oxide or nanoneedle oxide on the surface of the prepared metal foam.

\* \* \* \* \*